(12) United States Patent
de Kramer et al.

(10) Patent No.: US 6,475,479 B1
(45) Date of Patent: *Nov. 5, 2002

(54) TERPENES FOR REDUCING THE EFFECT OF PHEROMONE ON LEPIDOPTERA

(75) Inventors: Jacobus Jan de Kramer, Ettlingen (DE); Ulrich Neumann, Schifferstadt (DE); Ulrich Klein, Limburgerhof (DE); Mechtild Meiwald, Kaiserslautern (DE); Wolfgang Krieg, Weingarten (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,583

(22) PCT Filed: Jun. 3, 1996

(86) PCT No.: PCT/EP96/02391

§ 371 (c)(1),
(2), (4) Date: Dec. 2, 1997

(87) PCT Pub. No.: WO96/41527

PCT Pub. Date: Dec. 27, 1996

(30) Foreign Application Priority Data

Jun. 10, 1995 (DE) .......................... 195 20 706

(51) Int. Cl.⁷ .................. A01N 35/02; A01N 37/06; A01N 31/02

(52) U.S. Cl. ................ 424/84; 514/703; 514/546; 514/549; 514/552; 514/693; 514/724; 514/739; 514/919

(58) Field of Search .................. 424/84; 514/703, 514/546, 549, 552, 693, 724, 739, 919

(56) References Cited

U.S. PATENT DOCUMENTS

| 3,845,108 A | 10/1974 | Roelofs et al. ............. 260/488 |
| 4,049,828 A | 9/1977 | Cole ............................ 424/333 |
| 4,670,519 A | 6/1987 | Mueller ....................... 525/342 |

FOREIGN PATENT DOCUMENTS

| CA | 2111708 | 7/1992 |
| DE | 37 34 657 | 10/1987 |
| FR | 2678482 | 1/1993 |
| WO | 93/00805 | 1/1993 |
| WO | 93/00812 | 1/1993 |

OTHER PUBLICATIONS

CABA Abstract 76: 25603 (1975).*
AGricola abstract 95: 12219, abstracting Photochemistry and Photobiology, vol. 60(5), pp. 543–552 (1994).*
Roehrich et al., *Ann. Zool. Ecol. anim.*, vol. 11, No. 4, 1979, pp. 659–675.

* cited by examiner

Primary Examiner—John Pak
(74) Attorney, Agent, or Firm—Keil & Weinkauf

(57) ABSTRACT

The use of terpenes for reducing the pheromone action on Lepidoptera and a method which allows terpenes to act on the habitat of the Lepidoptera are described.

8 Claims, No Drawings

TERPENES FOR REDUCING THE EFFECT OF PHEROMONE ON LEPIDOPTERA

This application is a 371 of PCT/EP96/02391, filed on Jun. 3, 1996.

The present invention relates to the use of terpenes for reducing the pheromone action on Lepidoptera, and to a method which allows terpenes to act on the habitat of the Lepidoptera.

The use of pheromones, in particular mixtures of components of sex pheromones, in the control of Lepidoptera, which comprise harmful insects such as grape moths, codling moths, summer fruit tortrix moths, oriental fruit moths, cotton bollworms, peach twig borers, clearwing moths and leafworms, belongs to the prior art.

Sex pheromones are sex attractants which are produced and secreted into the environment, in the case of Lepidoptera, by female or male animals which are ready to mate and attract male or female Lepidoptera of the same type.

Fundamentally, there are three different possibilities of using sex attractants in crop protection:

pheromone traps, equipped with synthetic sex attractant lures, are suspended in potential areas of attack. The capture of male moths in the traps furnishes proof of the occurrence of this pest. It is an important aid in integrated crop protection for determining a suitable date for control using conventional methods (monitoring technique).

by combination of an attractant with insecticidal active compounds. There is the possibility of adding insecticides to the lure or the trap or else of treating only the immediate surroundings of the trap. The largest part of the male moth population attracted from a wide range can thus be killed (capture technique). The biotope loading is reduced to a justifiable extent.

by the method of saturating the airspace with sex attractants or similarly acting substances. The male butterflies are interrupted from finding the females and thus the mating of the animals is prevented. In this case, a relatively large amount of the attractant is distributed uniformly in the airspace in the total area of the plant crop to be protected such that the males can sense the presence of the attractant everywhere and their normal orientation behavior is disturbed.

Even in this last-mentioned procedure for the use of sex attractants, only comparatively small amounts of the active compounds, which often only correspond to fragments of the customary doses of the classic insecticidal active compounds, are needed. (Birch (ed.): Pheromones North Holland Publ. Co. (1974)). What is concerned here is an extremely selective, nontoxic control method with the greatest possible protection of the nontarget organisms, in particular the useful animals. However, the natural sex attractants which are produced by the appropriate organs of the female animals are often accessible with difficulty synthetically.

In a method for the prognosis of the occurrence of Lobesia, the Lobesia sex attractant E7,Z9-dodecadienyl-1-acetate, applied as lures in traps, is used in viticulture as described in DE Patent 24 40 759. Specific control of the grape berry moth has been possible in practice since 1994 using the known sex attractant E7,Z9-dodecadienyl-1-acetate.

Laboratory and small-scale experiments for affecting Lobesia botrana males by the confusion technique using the original sex attractant, E7,Z9-dodecadienyl-1-acetate, and using similar substances, namely Z9-dodecenyl-1-acetate, E7-dodecenyl-1-acetate and E7,E9-dodecadienyl-1-acetate, have been carried out with varying success (ROEHRICH et al., Ann. Zool. Ecol. quim. 1979, p. 659 ff. and the sources indicated there, GUREVITZ and GOTHILF, Phytoparasitica 10 p. 140 (1982)).

DE-C 36 03 377 describes a mixture of Z9-dodecenyl-1-acetate and E7-dodecenyl-1-acetate for controlling Lobesia botrana.

It is common to all the methods described that pheromones are always used which attract the Lepidoptera.

Helmut Snoek in Duftstoffe, p. 36, Eigenverlag 1992, describes another route by confusing the insect female with ethereal oils so that it does not find the test plant necessary for laying eggs. On p. 39, however, Helmut Snoek comes to the conclusion that large-area monocrops cannot be effectively protected by aromatic products.

It was an object of the present invention to make available further methods for controlling Lepidoptera effectively. Surprisingly, it has been found that the pheromone action on Lepidoptera can be reduced using terpenes.

Terpenes suitable for the present invention are acyclic, monocyclic and bicyclic terpenes, sesquiterpenes, diterpenes and mixtures thereof including E and Z isomers thereof or optical antipodes thereof.

Suitable acyclic terpenes include terpene hydrocarbons such as ocimene, myrcene, terpene alcohols such as geraniol, nerol, linalool, citronellol, nerolidol, prenol (dimethylallyl alcohol), tetrahydrolinalool, geranylgeraniol, 2,6-dimethylheptan-2-ol, terpene aldehydes such as citral, neral, citronellal, tetrahydrocitronellal (2,5,7,7-tetramethyloctanol), terpene ketones such as α-ionone, β-ionone, geranylacetone, phytol, isophytol, retinal and mixtures thereof.

Suitable monocyclic terpenes include monocyclic terpene hydrocarbons such as α-terpinene, γ-terpinene, terpinolene, α-phellandrene, β-phellandrene, limonene, dipentene, monocyclic terpene alcohols such as menthol, α-terpineol, 1,8-terpine, monocyclic terpene ketones such as menthone, pulegone, carvone and mixtures thereof.

Suitable bicyclic terpenes include the carane group with carane, carone and carvenone, the pinane group with pinane, α-pinene and β-pinene and the bornane group with bornane and camphor, and mixtures thereof.

Suitable sesquiterpenes include the acyclic sesquiterpenes such as farnesol, nerolidol, monocyclic sesquiterpenes such as bisabolene, bicyclic sesquiterpenes such as cadinene, β-selinene, tricyclic sesquiterpenes such as α-santalene, and mixtures thereof.

Suitable diterpenes include phytol, isophytol, retinal and mixtures thereof.

Those preferred are citral, nerolidol, prenol (dimethylallyl alcohol), tetrahydrolinalool, geranylgeraniol, 2,6-dimethylheptan-2-ol, neral, citronellal, tetrahydrocitronellal (2,5,7,7-tetramethyloctanol), geranylacetone, phytol, isophytol, retinal and mixtures thereof.

Those particularly preferred are citral, nerolidol, prenol (dimethylallyl alcohol), tetrahydrolinalool, geranylgeraniol, 2,6-dimethylheptan-2-ol, neral, citronellal, tetrahydrocitronellal (2,5,7,7-tetramethyloctanol), geranylacetone and mixtures thereof.

Those furthermore preferred are citral, neral, citronellal, tetrahydrocitronellal (2,5,7,7-tetramethyloctanol), geranylacetone and mixtures thereof.

In the context of the present invention, citral has proven to be very particularly effective.

Both liquid and solid preparations are suitable for formulation, according to the invention, of the terpenes.

Suitable solvents are high-boiling, aromatic, aliphatic or cycloaliphatic compounds. Beside hydrocarbons, esters, ethers, silicone oils or ketones are particularly highly suitable. Typical representatives of these classes are, for example: xylene, methylnaphthalenes, liquid paraffins, cyclohexanone, ethyl glycol acetate, isophorone and dibutyl phthalate. These solvents can be used on their own or as mixtures with other components. Solutions in vegetable, animal or synthetic oils or fats and other evaporation-inhibiting solvents of low vapor pressure, eg. higher $C_{10}$–$C_{20}$-alkyl acetates or straight-chain or branched $C_1$–$C_8$-dialkyl phthalates, can furthermore be prepared for the purposes of prolonging the action.

The terpenes can furthermore also be used as a mixture with pheromones and related aromatic substances. Suitable pheromones are described, for example, in Heinrich Arn, List of Sex Pheromones of Lepidoptera and Related Attractants, Organisation Internationale de Lutte Biologique Section Regionale Ouest Palearctique, 1986.

Examples of suitable pheromones are Z9-dodecenyl-1-acetate, Z8-dodecenyl-1-acetate, E7-dodecenyl-1-acetate, E5-decenyl-1-acetate, E5-decen-1-ol, E7,Z9-dodecadienyl-1-acetate, Z11-tetradecenyl-1-acetate, Z9-tetradecenyl-1-acetate, Z8-tetradecenyl-1-acetate, E8,E10-dodecadien-1-ol, Z3,Z13-octadecadienyl-1-acetate and E2,Z13-octadecadienyl-1-acetate.

If pheromones and related substances are additionally used, E7,Z9-dodecadienyl-1-acetate, Z9-dodecenyl-1-acetate, E7-dodecenyl-1-acetate and mixtures thereof are preferred.

If pheromones and related substances are additionally used, mixing weight ratios of terpene:pheromone of from 100:1 to 1:100, preferably 100:2 to 1:50 and particularly preferably 100:5 to 1:10, very particularly preferably 100:10 to 1:1, have proven suitable.

For application of the terpenes, dispensers are used which release the active compound over a long period with a constant release rate. Many such systems have already been described in the literature and can be arranged in two categories:

1. matrix systems
2. reservoir systems.

In matrix systems, the active compound is dispersed homogeneously in a matrix. The release rate, due to this means of construction, is nonlinear, but decreases with time. In the case of the reservoir systems, the active compound is situated in a reservoir and is given off by diffusion through a wall of constant thickness. In contrast to the matrix systems, reservoir systems therefore have a more constant release rate and are superior in release characteristics and often also in the duration of release.

In the case of the matrix systems, the terpenes are bound in or on natural or synthetic solid carriers such as rubber, cork, cellulose, plastics, ground carbon, wood meal, silicates, pumice grit, calcined clay or similar solid carriers. Reservoir systems include special capsule formulations, plastic containers, capillaries or other vessels, the active compound being evaporated through films or narrow openings, particularly uniform scent concentrations being achieved over relatively long periods. Multilayer platelets made of plastic or cellulose, flakes, are also suitable.

Suitable plastic containers are described in DE-A 36 40 880 and EP-A 496 102 and EP-A 540 932.

The terpene content in formulations can vary within wide limits. Generally, the ratio of terpene : additive can be, for example, in the range from, for example, 10:1 to 1:10³. In capsule formulations or other suitable containers, the terpene, for example, can be used in pure, undiluted form and its proportion by weight, based on the total formulation, can be very high and up to 90%. In general, however, very low active compound concentrations in the formulations are sufficient in order to exert the desired action on Lepidoptera. A quantitative ratio of terpene:additive of from 1:3 to 1:10² is preferred.

The terpenes can also be applied in comparatively high concentrations. For this method, formulations having poorly volatile additives which give off the terpenes over a sustained period are best suited, such as rubber, cellulose, wax, polymers or evaporation-inhibiting, poorly volatile oils or paraffins, and also formulations in capsules or other containers (capillaries) which give off the terpenes either through their wall or through narrow openings. The terpene concentration here is in general in the range from 1:1 to 1:10³.

EXAMPLE 1

Laboratory Wind Tunnel 4 electric traps up to 2 cm³ in size were installed in a laboratory wind tunnel. As electric traps, commercially available electric insect capture appliances were rebuilt to give recording lure traps. The fluorescent tube normally responsible for the attractant action was replaced by a scent source.

To avoid positional effects, the four traps were fixed. The wheel rim was rotated by means of a motor having a speed of two revolutions per hour (once around its own axis and back), so that the traps continuously changed position.

With the same lure a preference for certain traps was not found: downwind from 50 to 500 (depending on the directly available amount, as a rule from 200 to 300) Lobesia males of age from one to three days were set free, these flew specifically to the scent sources contained in the traps.

The number of moths trapped in each case was determined daily. By means of the number of moths trapped in the individual traps, the attractiveness of the particular lure was determined (preference test).

The influence of various dilutions of E7,Z9-dodecadien-1-yl acetate was determined by setting the number of moths in the most common trap equal to one; the capturing ability of the other traps was calculated relative to this.

The scent sources used were cartridges (single-use syringes made of polypropylene; content: 1 ml). Filter papers of edge length 4 mm×60 mm were impregnated with 30 μl of the respective test substance and placed in the syringes, which were then closed with an injection needle (0.9 mm external diameter).

A stream of air of velocity 67 ml/min was passed through these cartridges.

To investigate the action of terpenes, the recapture rate of the cartridges which were lured with 30 μl of E7,Z9-dodecadien-1-yl acetate in a concentration of $10^{-4}$ g/g of silicone oil as a standard or with the same amount of standard and citral in $10^{-1}$ g/g of silicone oil was compared.

The recapture rate is the ratio of the number of captured Lobesia males and the number of Lobesia males set free.

The recapture rate of the standard was set equal to one and that of the traps with the terpene additive was calculated relative to this.

For the traps with addition of citral, an inhibition of the recapture rate in the citral-containing cartridges of 90% resulted.

EXAMPLE 2

Outdoor Wind Tunnels

In spring 1994 two outdoor wind tunnels were built over a row of vines in each case in an experimental field of the SLFA Neustadt. These were aluminum scaffoldings 2 m high, 2 m wide and 10 m long.

The front and back were covered with mosquito nets made of cotton (mesh width 1.5×1.5 mm); 50µ thick polyethylene film lay over the entire length.

Air was blown into the interior through a ventilator at the front of the tunnel.

Two traps each were attached at a height of approximately 60 cm in the interior of the two wind tunnels on the ventilator side. The traps were lured with E7,Z9-dodecadien-1-yl acetate. Tunnel 1 remained untreated and served as a control. To simulate a mating disruption situation, 10 filter papers were uniformly distributed at various heights (20–120 cm) in tunnel 2 along the row of grapevines. 1 ml of citral solution in silicone oil with a dilution of $10^{-1}$ g/g was in each case added dropwise to these in order to achieve a uniform concentration of the substance in the interior. A specific number of Lobesia males were in each case set free on the sides of the two wind tunnels opposite to the ventilator sides. After the end of the experiment, the Lobesia males captured in the traps were counted and the recapture rate was determined.

|  | Recapture rate |
|---|---|
| Tunnel 1 (control) | 0.18 |
| Tunnel 2 (treatment with citral) | 0.01 |

This means an inhibition of the recapture rate by 94.5%.

We claim:

1. A method of disturbing the mating of Lepidoptera, which comprises reducing the pheromone action and thereby detracting the male species of Lepidoptera by treating the habitat of the Lepidoptera with an effective amount of citral and a pheromone and/or a pheromone related attractant.

2. The method of claim 1, wherein the citral is applied to the habitat as a mixture with an additive selected from the group consisting of the organic solvents, vegetable oils, animals oils, synthetic oils and mixtures thereof.

3. The method of claim 1, wherein the pheromone or the pheromone related attractant is selected from the group consisting of E7,Z9-dodecadienyl-1-acetate, Z9-dodecenyl-1-acetate, E7-dodecenyl-1-acetate, E7,Z9-dodecadien-1-ol, Z9-dodecen-1-ol, E7,Z9-dodecadien-1-al, Z9-dodecen-1-al and mixtures thereof.

4. The method of claim 1, wherein the pheromone and/or the pheromone related attractant is selected from the group consisting of E7,Z9-dodecadienyl-1-acetate, Z9-dodecenyl-1-acetate, E7-dodecenyl-1-acetate and mixtures thereof.

5. The method of claim 1, wherein citral and the pheromone and/or the pheromone related attractant is applied in a weight ratio of from 100:1 to 1:100.

6. The method of claim 5, wherein the weight ratio of citral to the pheromone and/or the pheromone related attractant is from 100:2 to 1:50.

7. The method of claim 5, wherein the weight ratio of citral to the pheromone and/or the pheromone related attractant is from 100:5 to 1:10.

8. The method of claim 5, wherein the weight ratio of citral to the pheromone and/or the pheromone related attractant is from 100:10 to 1:1.

* * * * *